US012213960B2

(12) United States Patent
Lee et al.

(10) Patent No.: US 12,213,960 B2
(45) Date of Patent: Feb. 4, 2025

(54) METHOD OF PREVENTING OR IMPROVING UV-INDUCED SKIN DAMAGE USING HYDROANGENOL AS ACTIVE INGREDIENT

(71) Applicant: COSMAXBIO CO., LTD., Jecheon-si (KR)

(72) Inventors: Sun Hee Lee, Seongnam-si (KR); Keun Suk Lee, Hanam-si (KR); Hyoun Jea Kim, Yongin-si (KR); Yu Kyong Shin, Yongin-si (KR); Hye Shin Ahn, Bucheon-si (KR); Kyung Tae Lee, Seoul (KR); Ji Sun Shin, Seoul (KR)

(73) Assignee: COSMAXBIO CO., LTD., Jecheon-si (KR)

( * ) Notice: Subject to any disclaimer, the term of this patent is extended or adjusted under 35 U.S.C. 154(b) by 1003 days.

(21) Appl. No.: 17/196,513

(22) Filed: Mar. 9, 2021

(65) Prior Publication Data

US 2021/0196677 A1    Jul. 1, 2021

Related U.S. Application Data

(63) Continuation-in-part of application No. 16/772,471, filed as application No. PCT/KR2018/004922 on Apr. 27, 2018, now abandoned.

(30) Foreign Application Priority Data

Dec. 19, 2017    (KR) .................. 10-2017-0175385

(51) Int. Cl.
*A61K 31/366* (2006.01)
*A23L 33/105* (2016.01)
*A61K 8/49* (2006.01)
*A61K 8/9789* (2017.01)
*A61K 9/00* (2006.01)
*A61K 36/185* (2006.01)
*A61Q 19/00* (2006.01)
*A61Q 19/08* (2006.01)

(52) U.S. Cl.
CPC .......... *A61K 31/366* (2013.01); *A23L 33/105* (2016.08); *A61K 8/498* (2013.01); *A61K 8/9789* (2017.08); *A61K 9/0019* (2013.01); *A61K 9/0053* (2013.01); *A61K 36/185* (2013.01); *A61Q 19/004* (2013.01); *A61Q 19/08* (2013.01); *A61K 2236/333* (2013.01); *A61K 2236/39* (2013.01); *A61K 2236/53* (2013.01); *A61K 2800/92* (2013.01)

(58) Field of Classification Search
None
See application file for complete search history.

(56) References Cited

U.S. PATENT DOCUMENTS

2016/0074315 A1    3/2016    Caetano et al.

FOREIGN PATENT DOCUMENTS

| JP | 2000007546 | 1/2000 |
| JP | 2002029934 | 1/2002 |
| JP | 2003192566 | 7/2003 |
| KR | 20010057585 | 7/2001 |
| KR | 20090081178 | 7/2009 |
| KR | 20170132388 | 12/2017 |

OTHER PUBLICATIONS

International Search Report—PCT/KR2018/004922 dated Sep. 13, 2018.
Kim, et al., Hydrangenol inhibits lipopolysaccharide-induced nitric oxide production in BV2 microglial cells by suppressing the NF-KB pathway and activating the Nrf2-mediated HO-1 pathway, International Immunopharmacology, vol. 35, 2016, pp. 61-69.
Yoshikawa, et al., Development of Bioactive Functions in Hydrangeae Dulcis Folium. V. On the Antiallergic and Antimicrobial Principles of Hydrangeae Dulcis Folium. (2). Thunberginols C, D, and E, Thunberginol G 3'-O-Glucoside, (−)-Hydrangenol 4'-O-Glucoside, and (+)-Hydrangenol 4'-O-Glucoside, Chem. Pharm. Bull., vol. 44, No. 8, 1996, pp. 1440-1447.

*Primary Examiner* — Nannette Holloman
(74) *Attorney, Agent, or Firm* — CANTOR COLBURN LLP

(57) ABSTRACT

Provided is a method for preventing or improving UV-induced skin damage of a subject in need thereof, which comprises administering to the subject an effective amount of a composition containing hydrangenol derived from the extract of *Hydrangea serrata* as an active ingredient. The composition containing hydrangenol derived from the extract of *Hydrangea serrata* is able to increase secretion of hyaluronic acid and procollagen type-1 and inhibit secretion of MMP-1 in skin cells, and therefore effective in preventing or improving UV-induced damage of skin cells. Accordingly, the hydrangenol-containing composition is usefully available as a quasi-drug, drug, food, or cosmetic composition.

8 Claims, 25 Drawing Sheets

METHOD OF PREVENTING OR IMPROVING UV-INDUCED SKIN DAMAGE USING HYDROANGENOL AS ACTIVE INGREDIENT

TECHNICAL FIELD

The present t invention relates to a composition for preventing or improving UV-induced skin damage, and more particularly to a method for preventing or improving UV-induced skin damage of a subject in need thereof, which comprises administering to the subject an effective amount of a composition containing hydrangenol derived from the extract of *Hydrangea serrata* as an active ingredient.

BACKGROUND ART

Skin aging is categorized into extrinsic and intrinsic aging depending on what factors contribute to aging. Intrinsic aging is affected by the age-dependent decline of the physiologic functions of the dermis and the epidermis. Extrinsic aging is caused by the degenerative change of the physiologic functions of the skin attributable to the environmental factors, such as air pollution, UV exposure, stress, etc. In the mechanism of skin aging, UV-induced oxidative stress increases the production of free radicals in the body and accelerates the activation of MMP-1 and hyaluronidase, which are responsible for degradation of collagen and hyaluronic acid, respectively, resulting in damage to the epidermis and dermis.

Sun exposure happens all the time in daily life. Especially, UV-B exposure causing cell damage and skin cancer is an inevitable part of life. Therefore, many studies have recently been made on the materials having physiological efficacy/effect in preventing or improving UV-induced skin cell damage.

*Hydrangea serrata* is a broad-leaved dwarf species of plant in the family Hydrageaceae, of which the leaf is an edible part as found in the list of food materials according to the National Institute of Food and Drug Safety Evaluation (NIFDSE) in South Korea. The leaf is called "Gynostemma pentaphyllum (Chilyeopdam)" as an herb of the oriental medicine and has long been used for treatment of chronic bronchitis, relief of cough and phlegm, anti-inflammation, detoxification, etc.

Hydrangenol is a component mostly found in *Hydrangea serrata* (JP2002-029934); molecular weight: 256.25 g/mol, IUPAC name: 8-hydroxy-3-(4-hydroxyphenyl)-3,4-dihydroisochromen-1-one. Its derivatives are (−)-hydrangenol 4'-O-glucoside and (+)-hydrangenol 4'-O-glucoside. Hydrangenol is reported to have functions of skin whitening (JP2000-007546) and anti-inflammation (Kim, H. J, et al., Hydrangenol inhibits lipopolysaccharide-induced nitric oxide production in BV2 microglial cells by suppressing the NF-κB pathway and activating the Nrf2-mediated HO-1 pathway, International Immunopharmacology Vol. 35, pp. 61-69, 2016, 1567-5679).

The uses of hydrangenol for preventing or improving UV-induced skin damage are not yet known, and the related mechanisms have never been studied. The inventors of the present invention have performed research on the fundamental efficacy of hydrangenol to accelerate the activation of antioxidant enzymes against UV radiation and inhibit the UV-induced damage of the epidermis and dermis of the human skin.

In an attempt to solve the problems with the prior art, the inventors of the present invention have found the fact that a composition containing hydrangenol derived from the extract of *Hydrangea serrata* as an active ingredient is able to increase secretion of hyaluronic acid and procollagen Type 1 in the epidermis and dermis of the human skin and that a reduction of MMP-1 improves the skin damage by preventing UVB-induced skin damage.

CITED DOCUMENTS

Patent Document 1: JP2000-007546 A
Patent Document 2: JP2002-029934 A

DISCLOSURE OF INVENTION

Technical Problem

It is therefore an object of the present invention to provide a composition containing hydrangenol derived from the extract of *Hydrangea serrata* as an active ingredient for preventing or improving UV-induced skin damage.

Further, it is another object of the present invention to provide a method for preventing or improving UV-induced skin damage which comprises administering an effective amount of hydrangenol to a subject in need thereof.

Technical Solution

In one aspect of the present invention, there is provided a method for preventing or improving UV-induced skin damage of a subject in need thereof, which comprises administering an effective amount of a composition containing hydrangenol represented by the following chemical formula 1 as an active ingredient:

[Chemical Formula 1]

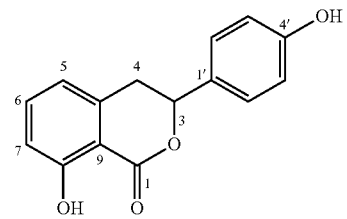

In the method of the present invention, the skin damage is UV-induced damage to epidermal and dermal cells in human skin. As demonstrated in the experimental examples of the present invention, hydrangenol accelerates proliferation or recovery of the epidermal and dermal cells damaged by UV radiation, reduces production of MMP-1, and increases production of procollagen and hyaluronic acid, thereby exerting preventive, improving or therapeutic effects for the UV-induced skin damage.

Throughout this specification, the term "skin damage" inclusively refers to UV-induced skin damage in human body, such as cell death in the skin, DNA damage of skin cells, an increase in the level of reactive oxygen species or lipid peroxidation, and so forth. The symptoms of the skin damage may include blemishes, sunburn, impaired pigmentation, photoaging, skin cancer, etc. The term "prevention of damage" is understood to include all actions to suppress or delay the damage of skin cells caused by the UV exposure. Further, the term "improvement of damage" is understood to include all actions to alleviate the UV-induced damage of skin cells or reduce the severity of the related symptoms.

Further, the term "treatment of damage" is understood to include all actions to restore the UV-induced damage of skin cells to a previous normal skin condition. In the present invention, the term "improvement" of damage is understood to include "treatment" of damage in the broad sense.

In the method of the present invention, the hydrangenol may be commercially available or prepared from natural substances by separation and purification. The present invention provides a composition for preventing or improving UV-induced skin damage, where hydrangenol is preferably isolated from an extract of *Hydrangea serrata*. The *Hydrangea serrata* may be at least one selected from the group consisting of the whole, woody root, stem, branch, leaf, seed, and fruit of *Hydrangea serrata*. Preferably, the *Hydrangea serrata* may be the leaf of *Hydrangea serrata*.

In the method of the present invention, the extract of *Hydrangea serrata* may be obtained by any conventional extraction method for extracting a natural plant, such as hot water extraction, solvent extraction, distillation extraction, supercritical extraction, etc. Preferably, the extract of *Hydrangea serrata* is obtained by extraction with water, an organic solvent, or a combination of both. The organic solvent may be at least one selected from the group consisting of alcohols having 1 to 4 carbon atoms, such as ethanol, methanol, isopropanol, and butanol; preferably ethanol; and more preferably fermentation ethyl alcohol (Refer to Example 1).

In the method of the present invention, the hydrangenol is a fraction of the extract of *Hydrangea serrata*. Preferably, it is a fraction obtained from the extract of *Hydrangea serrata* in ethanol through separation and purification using ion-exchange chromatography (e.g., Diaion HP-20) and size exclusion chromatography (e.g., Sephadex LH-20) in sequence (Refer to FIG. 1). The fraction is recrystallized in methanol to yield a pure amorphous compound, hydrangenol.

In an example of the present invention, the substance obtained from the extract of *Hydrangea serrata* through separation and purification is identified as hydrangenol having the following chemical formula 1 according to the mass analysis (ESIMS) and NMR analysis (1H-NMR, 13C-NMR, DEPT NMR, HSQC NMR, HMBC NMR).

[Chemical Formula 1]

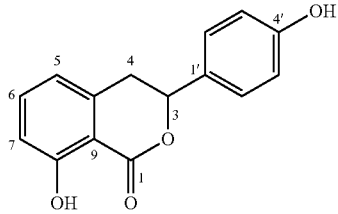

In the method of the present invention, the hydrangenol is contained in an amount of 0.0001 to 10 wt. % with respect to the total weight of the composition.

In the method of the present invention, the hydrangenol accelerates proliferation of skin cells damaged by UV radiation, reduces production of MMP-1, and increases production of procollagen and hyaluronic acid.

In the method of the present invention, the composition is used to moisturize the skin irritated by UV radiation or improve wrinkles. According to an example of the present invention, the efficacy of the hydrangenol to reduce the production of MMP-1 and promote the production of procollagen and hyaluronic acid indicates that the composition of the present invention can be used not only to prevent or improve UV-induced skin damage, but to moisturize the skin irritated by UV radiation or improve wrinkles of the skin.

According to experimental examples of the present invention, it is implied that the hydrangenol derived from *Hydrangea serrata* is capable of preventing and improving skin damage caused by UV-B exposure (Refer to Experimental Examples 1 to 4).

In the method of the present invention, the composition is for oral administration and has at least one dosage form selected from the group consisting of tablet, granule, pill, capsule, liquid, chewable gel, and gum.

In the method fo the present invention, the composition is for topical administration on the skin and has at least one dosage form selected from the group consisting of toner, essence, nutrition cream, moisturizing cream, gel, lotion, and ointment.

The composition containing hydrangenol derived from the extract of *Hydrangea serrata* as an active ingredient according to the present invention may be used for various applications: for example, quasi-drug compositions, cosmetic compositions, pharmaceutical compositions, health functional food compositions, etc.

The cosmetic compositions according to the present invention may further include at least one cosmetically acceptable carrier mixed with a general skin cosmetic. Common compositions for the carrier may include, but are not limited to, oils, water, surfactants, humectants, lower alcohols, thickening agents, chelating agents, colorants, preservatives, or fragrances, which may be appropriately used in combination.

The pharmaceutical compositions or the health functional food compositions according to the present invention may further include carriers, excipients or diluents that are generally used in the preparation of pharmaceutical compositions. The pharmaceutically acceptable carriers, excipients or diluents may include, but are not limited to, at least one selected from the group consisting of lactose, dextrose, sucrose, calcium silicate, cellulose, methylcellulose, amorphous cellulose, polyvinyl pyrrolidone, water, methyl hydroxybenzoate, propyl hydroxybenzoate, talc, magnesium stearate, and mineral oil.

The effective amount of the composition of the present invention may vary depending on the formulation method, the method, timing, and/or route of administration, and so forth. It may also be dependent upon various factors, including the type and intensity of the reaction intended by the administration of the composition, the subject's type, age, weight, health status, or gender, symptoms or severity of disease, gender, diet, excretion, and the ingredients of another drug composition medicated to the same subject in a simultaneous or asynchronous manner, etc. and similar factors known in the field of medicines. It may be possible for those skilled in the art to determine the effective amount appropriate to acquiring the desired therapeutic effects. The composition of the present invention may be administered once or multiple times daily. Accordingly, the dosage is not construed to limit the scope of the present invention. The preferred dosage of the pharmaceutical composition of the present invention is ranging from 0.01 µg/kg/day to 20,000 µg/kg/day, more specifically from 1 µg/kg/day to 10,000 µg/kg/day.

Effects of Invention

As described above, the composition containing hydrangenol derived from the extract of *Hydrangea serrata* according to the present invention inhibits secretion of MMP-1 produced by UV-B exposure and promotes secretion of hyaluronic acid and procollagen to prevent UV-induced skin damage and maintain elasticity of the skin. Therefore, the composition of the present invention can be usefully applied as a drug, food, or cosmetic composition.

BEST MODES FOR CARRYING OUT THE INVENTION

Hereinafter, the present invention will be described in further detail with reference to examples. It will be obvious to those skilled in the art that these examples are illustrative purposes only and are not construed to limit the scope of the present invention.

Example 1: Preparation of Extract of *Hydrangea Serrata*

The extract of *Hydrangea serrata* in the composition of the present invention was prepared in the following steps. Firstly, leaves of *Hydrangea* serrate were botanized in Jeju Island (South Korea), dried out for 4-5 days, and chopped to obtain a material for extraction. 25 g of chopped *Hydrangea serrata* was subjected to reflux extraction in hot water and 175 ml (7-fold, v/v) of ethanol (30%, 50%, 70%) at 50° C. for 3 hours. The product obtained by extraction was removed of insoluble substances through a Whatman (No 2.) extractant filter paper. Then, the product was concentrated under reduced pressure in a distillation apparatus equipped with a condenser and completely removed of the solvent. The extract of *Hydrangea serrata* thus obtained was dried out to an extraction yield of 20%.

Example 2: Preparation of Hydrangenol Derived from Extract of *Hydrangea Serrata*

Figure 1:
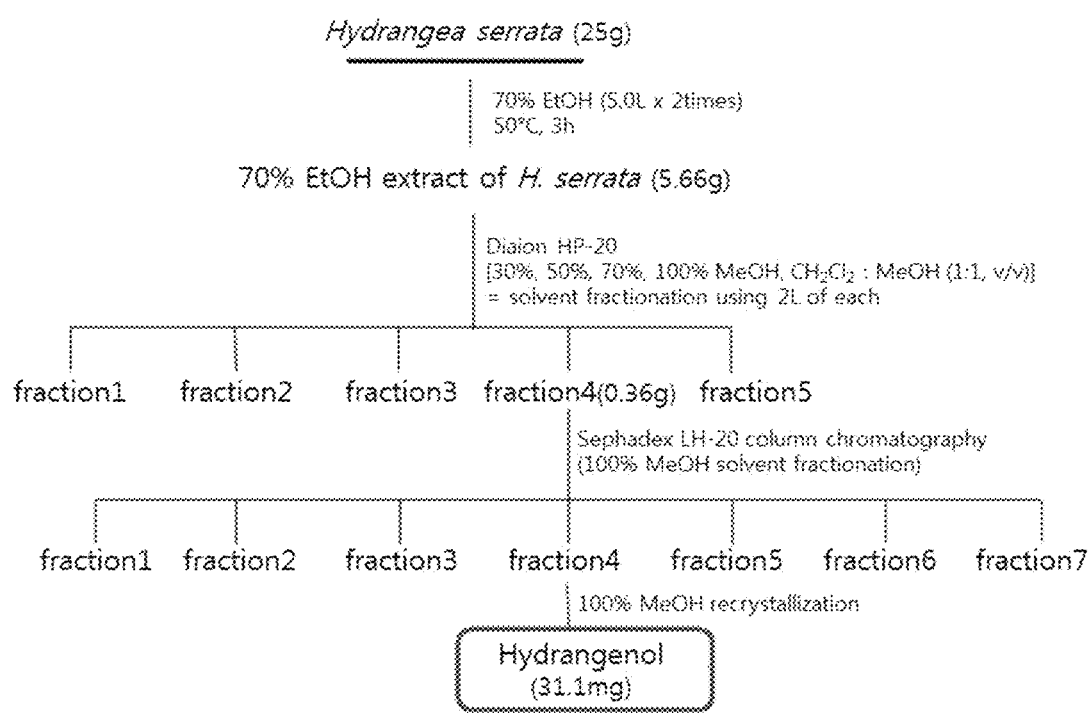
FIG. 1 is a schematic diagram showing the separation and purification process of preparing hydrangenol from the leaves of *Hydrangea serrata*.
Figure 2:
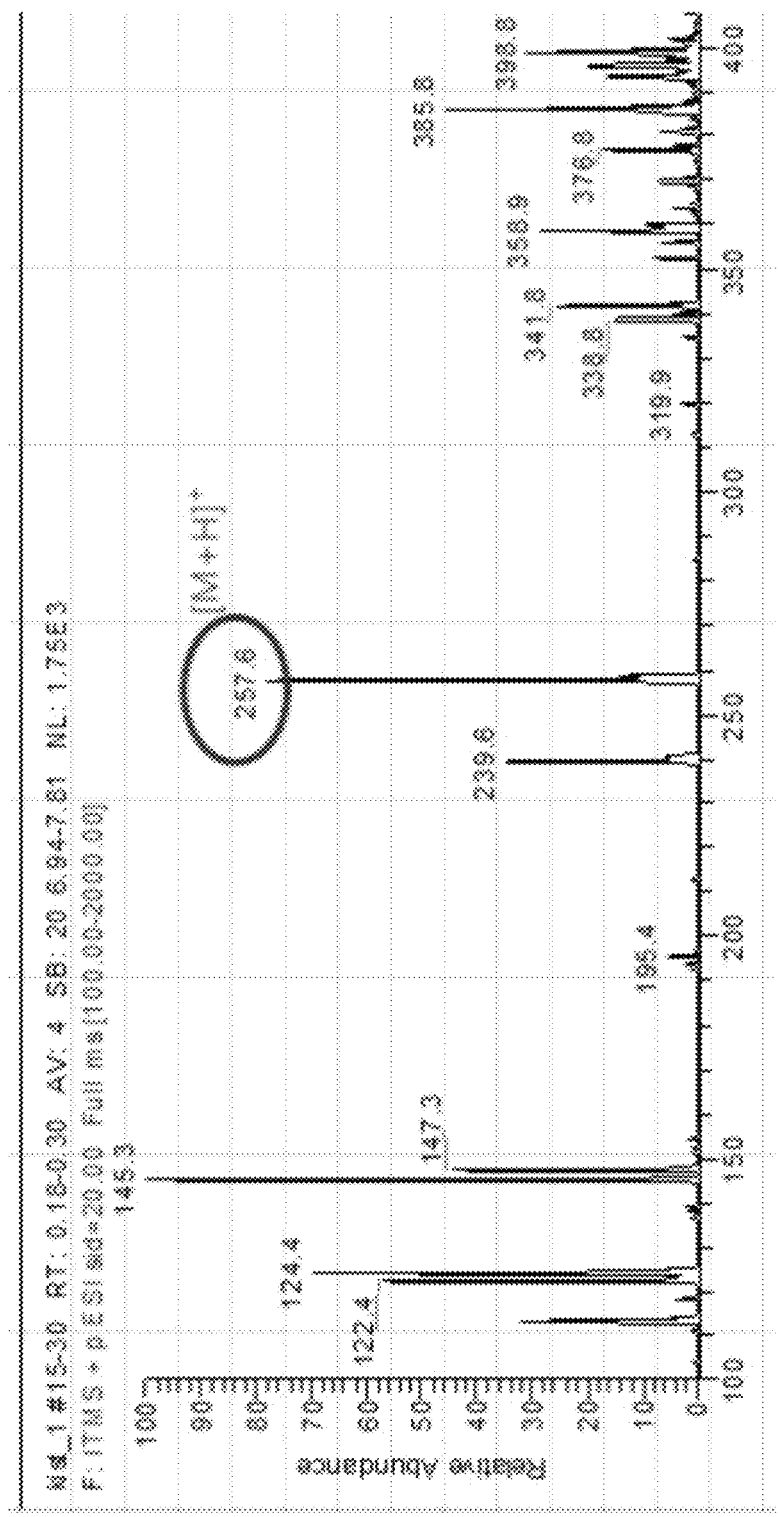
FIG. 2 is an ESIMS (positive-ion mode) spectrum of hydrangenol.
Figure 3:
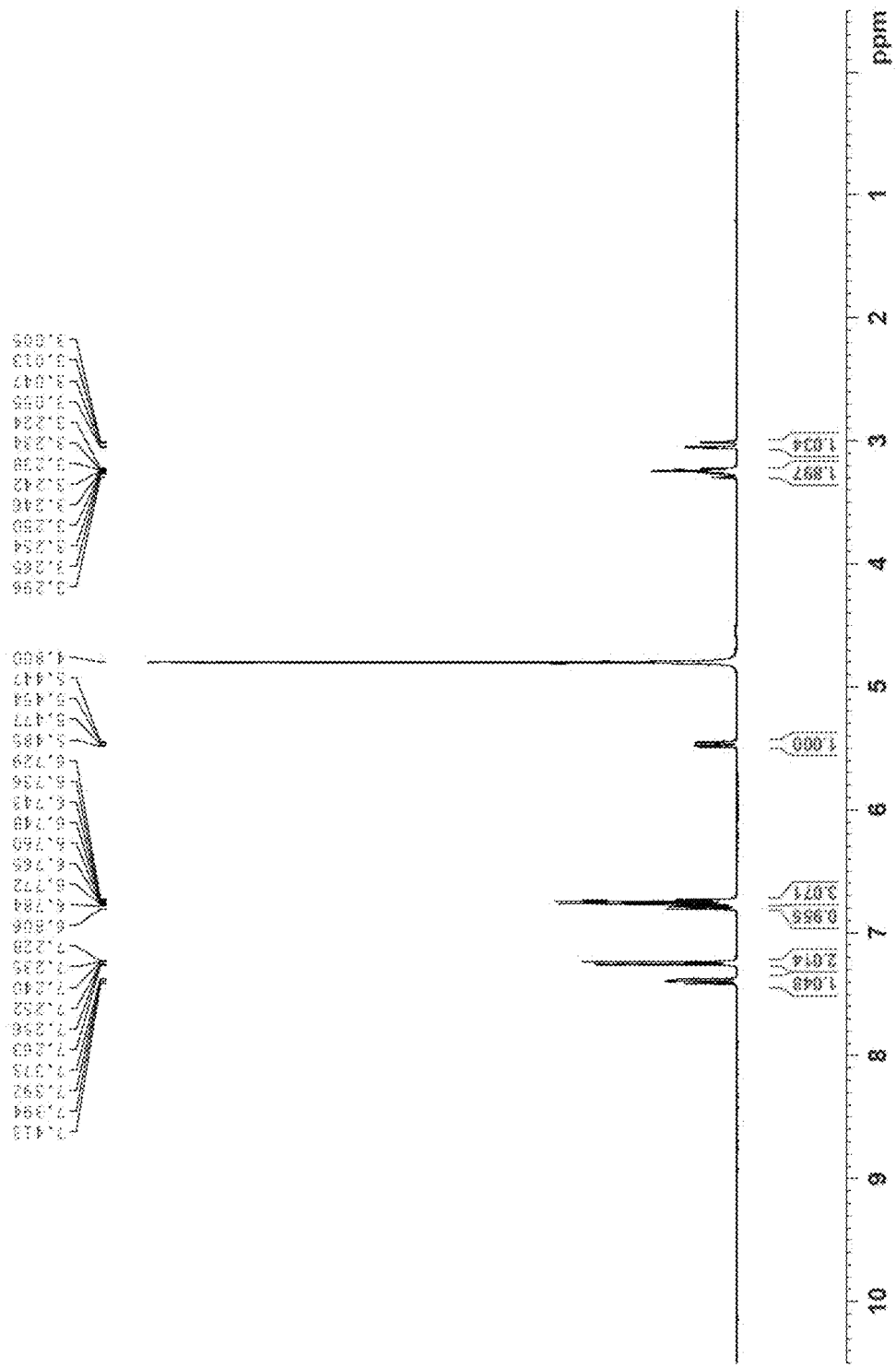
FIG. 3 is a 1H-NMR spectrum of hydrangenol.

5.66 g of the 70% ethanol extract obtained in Example 1 was subjected to a gel filtration with a Diaion HP-20. Each 2 L of the mixed solution of methanol (30%, 50%, 70%, 100%) and $CH_2Cl_2$-MeOH (1:1, v/v) was used as a developing solvent for solvent fractionation into five subfractions (392-70EDia 1~5). The subfraction 392-70EDia4 (357.4 mg) was solvent-fractionized with Sephadex LH-20 and a developing solvent of methanol into seven subfractions (392-70EDia4a~4g). The 392-70EDia4d subfraction was recrystallized in methanol to yield 31.1 mg of an amorphous compound 1 (hydrangenol). An ESIMS (positive-ion mode) analysis was conducted to identify the structure of the product in Example 2 revealed that m/z=257 $[M+H]^+$ (Refer to FIG. 2). As can be seen from the $^1$H-NMR spectrum (Refer to FIG. 3), in strong magnetic field, the methane proton (H-3) at δ H 5.50 formed a vicinal coupling with the methylene proton (H-4) at δ H 3.30 and 3.06. The chemical shift value as well as the vicinal coupling rendered the protons originated from the C-ring. As for the protons originated from the p-substituted benzene ring of a B-ring, the peaks H-2' and H-3' and the peaks H-6' and H-5' formed an ortho-coupling and showed up as a doublet (J=8.4 Hz); and the peaks H-2' and H-6' and the peaks H-3' and H-5' also formed an ortho-coupling and showed up as a doublet. This indicated the chemical structure rendered symmetric with respect to the hydroxyl group. In the 1, 2, 3-trisubstituted benzene of the A-ring, the protons H-5 and H-7 independently formed a coupling with the proton H-6, and an ortho-coupling was formed between the protons H-5 and H-7, which appeared as a doublet. The proton H-6 made an ortho-coupling and a meta-coupling and showed up as a double of doublets. This revealed that all the peaks corresponded to one proton.

Figure 4:
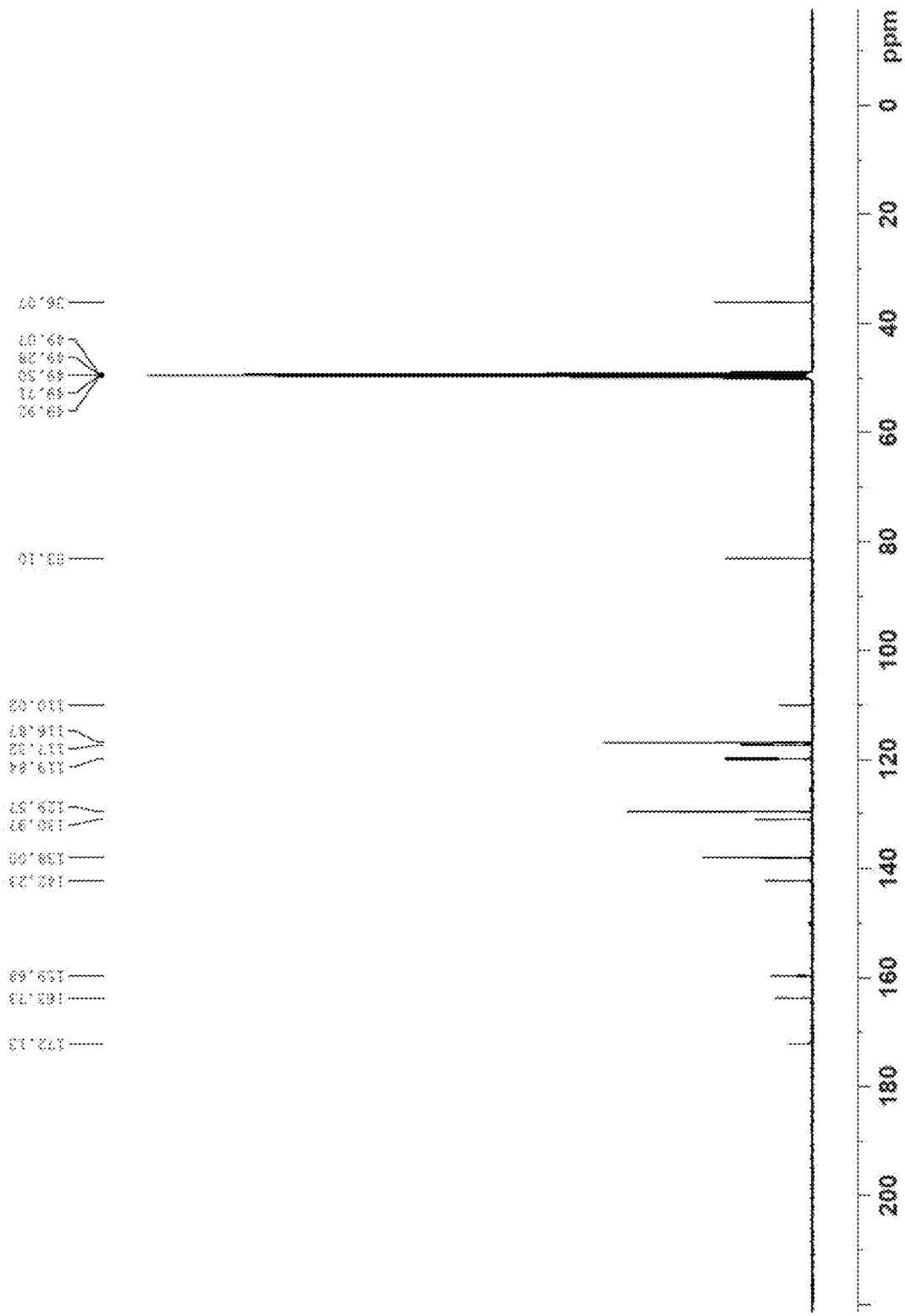
FIG. 4 is a 13C-NMR spectrum of hydrangenol.
Figure 5:
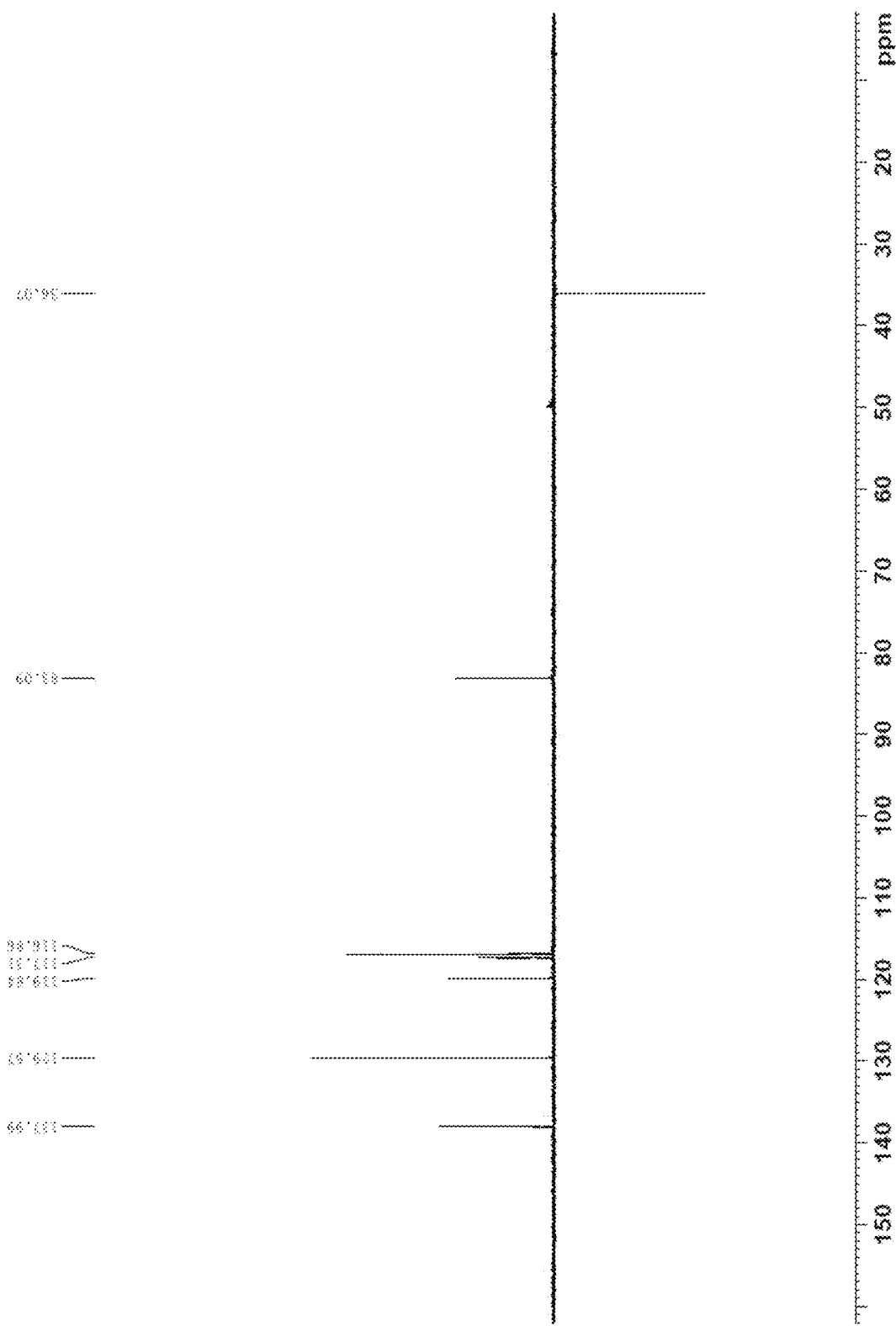
FIG. 5 is a DEPT NMR spectrum of hydrangenol.

In the $^{13}$C-NMR spectrum (Refer to FIG. 4), fifteen peaks including a para-substituent appeared. The quaternary carbon peak at δ C 172 was originated from the first carbon of the compound, that is, the carbonyl group; the peaks at δ C 116.9 (C-3', C-5') and δ C 129.6 (C-2', C-6') were originated from the para-substituent of an aromatic ring; and the peaks at δ C 36.1 and δ C 83.1 were originated from an aliphatic carbon and an oxygenated carbon, respectively. In the DEPT NMR spectrum (Refer to FIG. 5), seven protonated carbons were identified and the peak at δ C 36.1 was a methylene group originated from the C-4.

Figure 6:
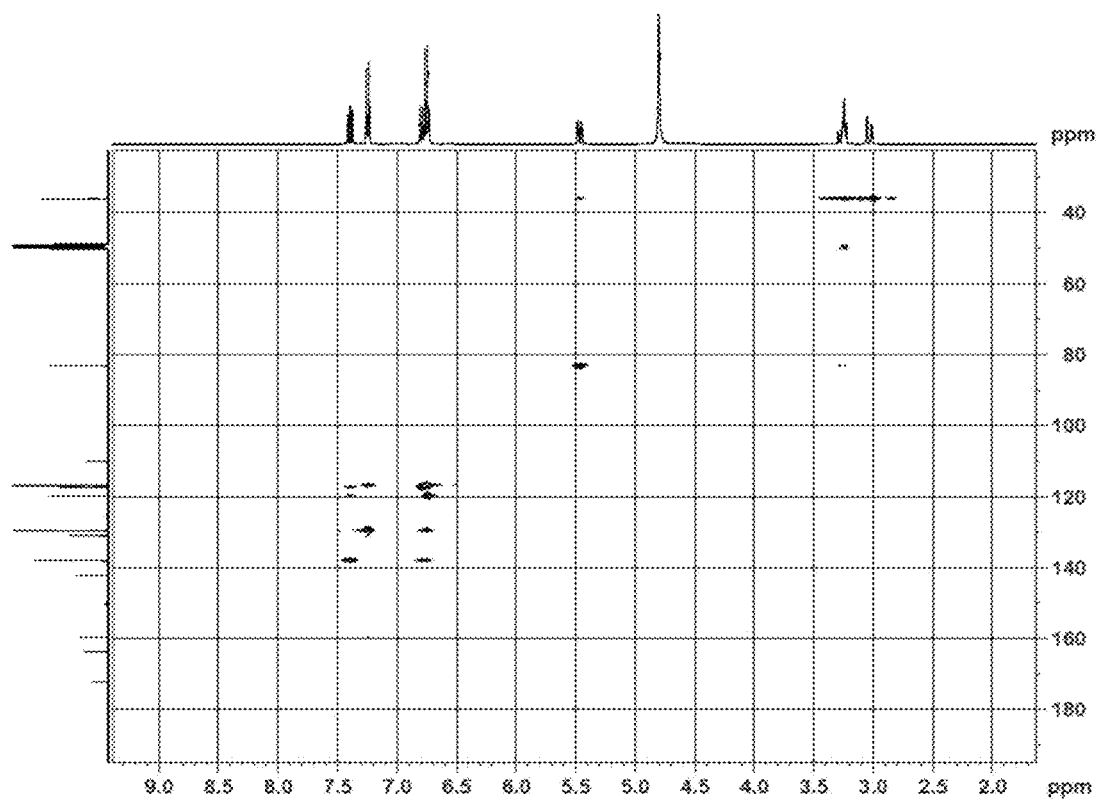
FIG. 6 is a HSQC NMR spectrum of hydrangenol.
Figure 7:
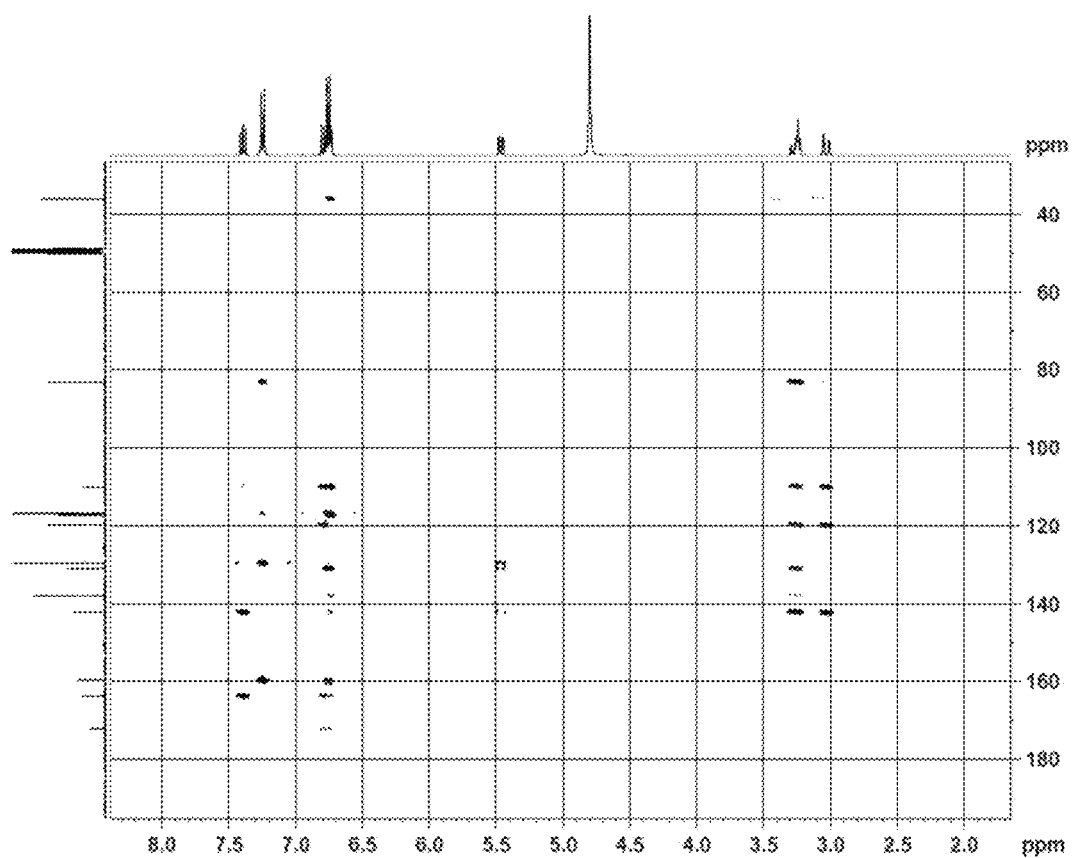
FIG. 7 is a HMBC NMR spectrum of hydrangenol.
Figure 8A:
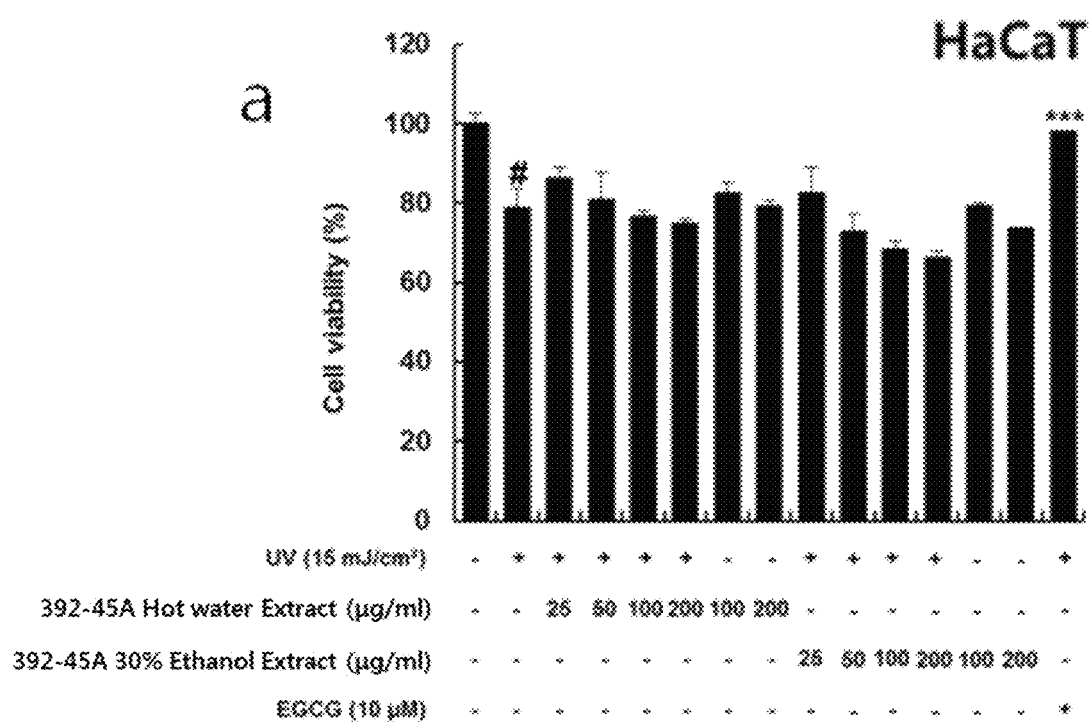
FIGS. 8A to 8D are a graph comparing the cell proliferation rate of the solvent-specific extract of *Hydrangea* serrate in epidermal and dermal cells with UV-induced damage (392-45A: *Hydrangea serrata*, EGCG: positive control, HaCaT: epidermal cell, and Hs68: dermal cell).
Figure 8B:
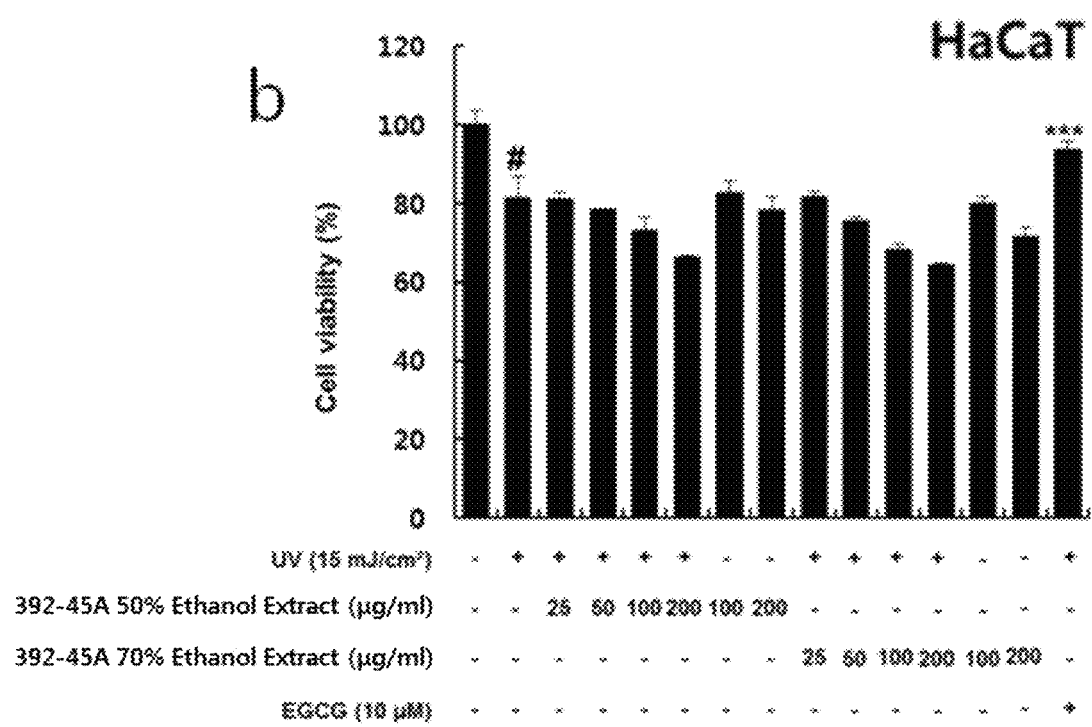
Figure 8C:
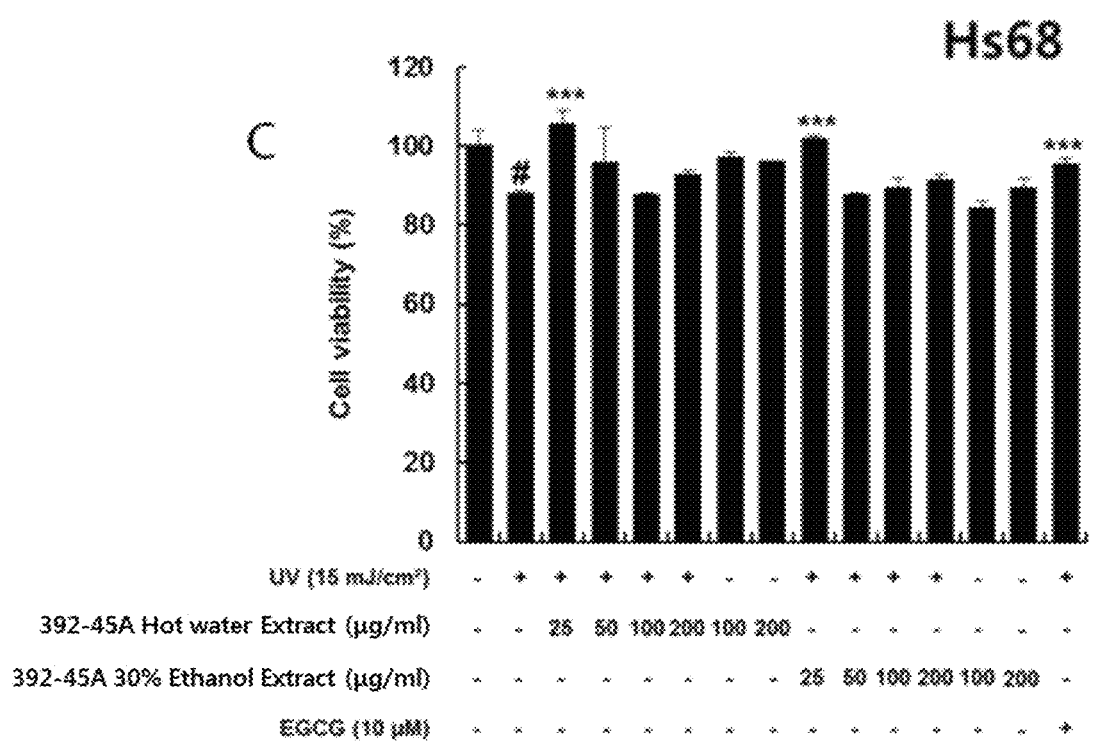
Figure 8D:
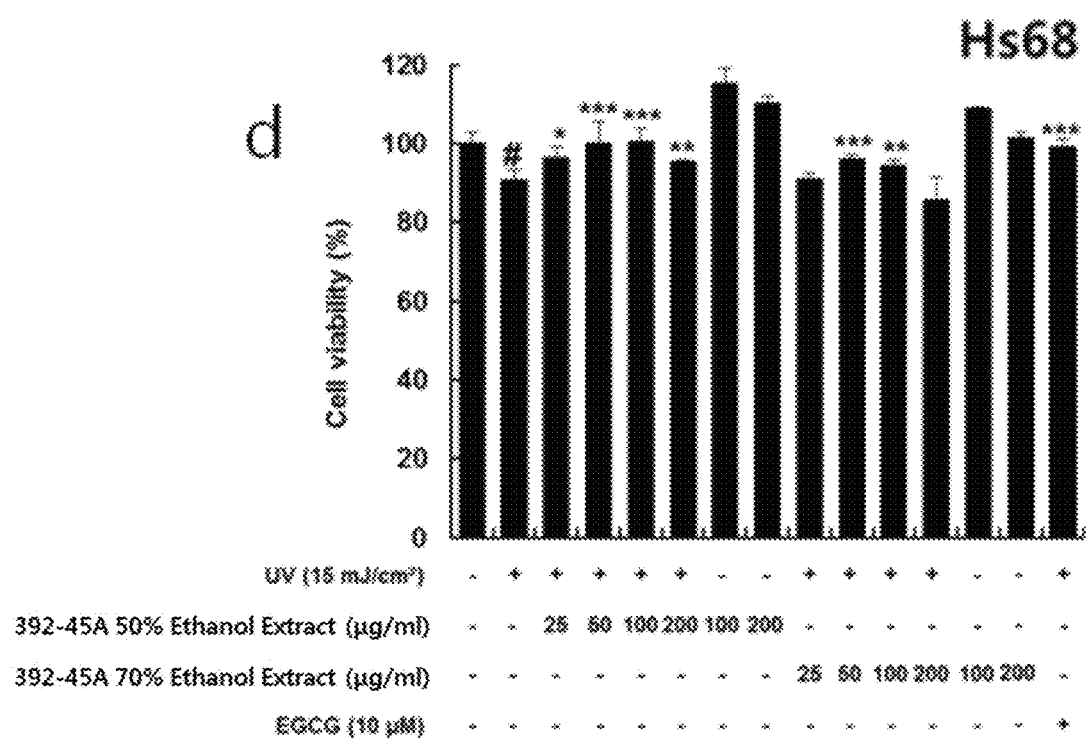

A 2D NMR analysis was carried out to analyze the precise structures of the peaks. The precise positions of the peaks were addressed according to the HSQC (Refer to FIG. 6), and the bonding positions of substituents were determined from the HMBC (Refer to FIG. 7). That is, the peak at δ H 7.26 (2H, d, J=8.4 Hz, H-2', 6') had a correlation with C-4 at δ C 36.1; whereas the peaks at δ H 3.06 and δ H 3.30 originated from H-4 had a correlation with the peaks at δ C 83.1 (C-3), δ c 119.8 (C-5), δ C 110.0 (C-9), and δ C 142.2 (C-10). A summary of the results and a comparison with the literatures identified the compound of Example 2 as hydrangenol (Yoshikawa M., Matsuda H., Shimoda H., Shimada H., Harada E., Naitoh Y., Miki A., Yamahara J., Murakami N. Development of Bioactive Functions in Hydrangeae *Dulcis* Folium. V. On the Antiallergic and Antimicrobial Principles of *Hydrangeae Dulcis* Folium. (2). Thunberginols C, D, and E, Thunberginol G 3'-O-Glucoside, (−)-Hydrangenol 4'-O-Glucoside, and (+)-Hydrangenol 4'-O-Glucoside. Chem. Pharm. Bull. 1996, 44:1440-1447).

Experimental Example 1: Effect of Hydrangenol on Proliferation of Cells with UV-Induced Damage Samples obtained in Examples 1 and 2 were measured in regards to the effect in recovering the skin damaged from UV-B exposure. In this experiment, HaCaT keratinocytes and HS68 fibroblasts were used as epidermal and dermal cells, respectively. In order to evaluate the possible efficacy of each sample in preventing or improving the UV-induced damage of skin cells, the cells were seeded into a 96-well microplate at a density of $1.0 \times 10^4$ cells/well and stabilized for 24 hours. Next, the culture medium was exchanged to a new one supplemented with the sample, and the cells were incubated for 24 hours. For UV-B irradiation, the culture medium was removed, washed with PBS, and exposed to UV-B radiation at 15 $mJ/cm^2$. After an incubation of 24 hours in a culture medium supplemented with the sample, the cells were subjected to an MTT assay to measure cell viability. The MTT assay measures the reduction of a tetrazolium component (MTT) into a formazan product by the mitochondria of viable cells. More specifically, 50 μl of a 5 mg/ml MTT solution was added to the cells, and after an incubation of 4 hours, the culture solution was completely removed and cells were dissolved in DMSO. The absorbance of the DMSO solution in the microplate was quantified by spectrophotometry at 540 nm.

Figure 9:
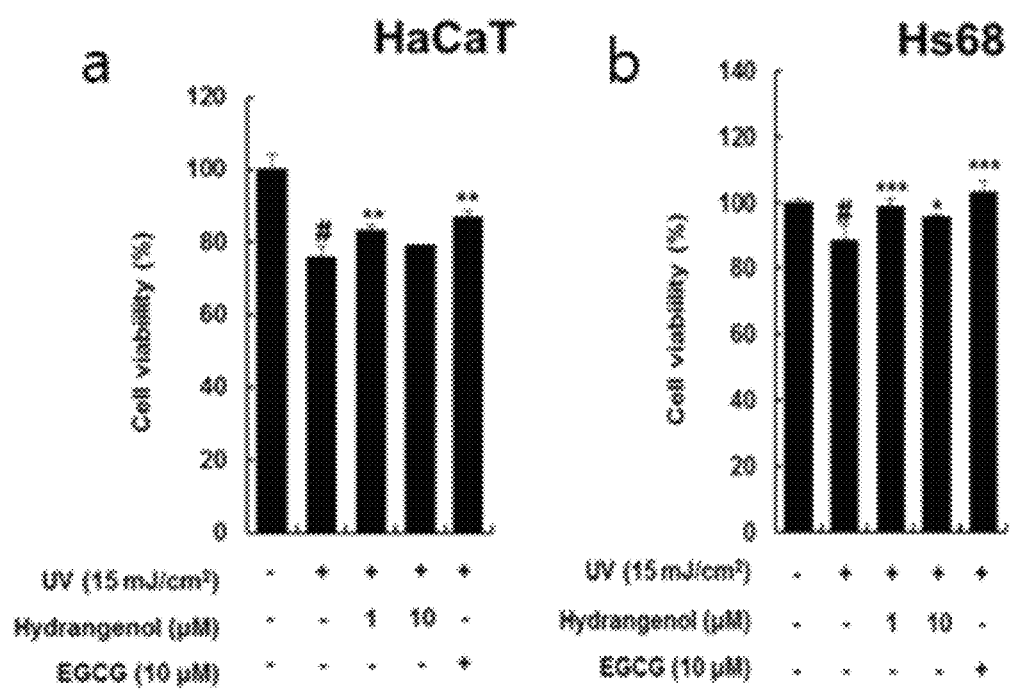
FIG. 9 is a graph showing the cell proliferation rate of hydrangenol in epidermal and dermal cells with UV-induced damage.
Figure 10A:
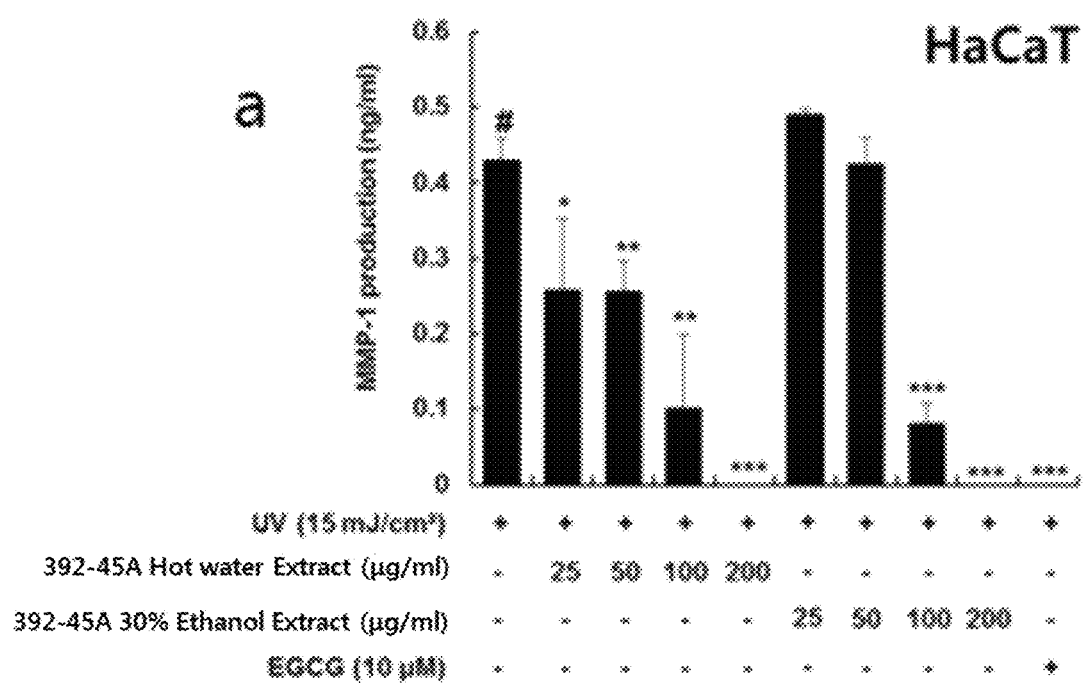
FIGS. 10A to 10D are a graph comparing the inhibitory effect of the solvent-specific extracts of *Hydrangea serrata* against MMP-1 in epidermal and dermal cells damaged by UV exposure.
Figure 10B:
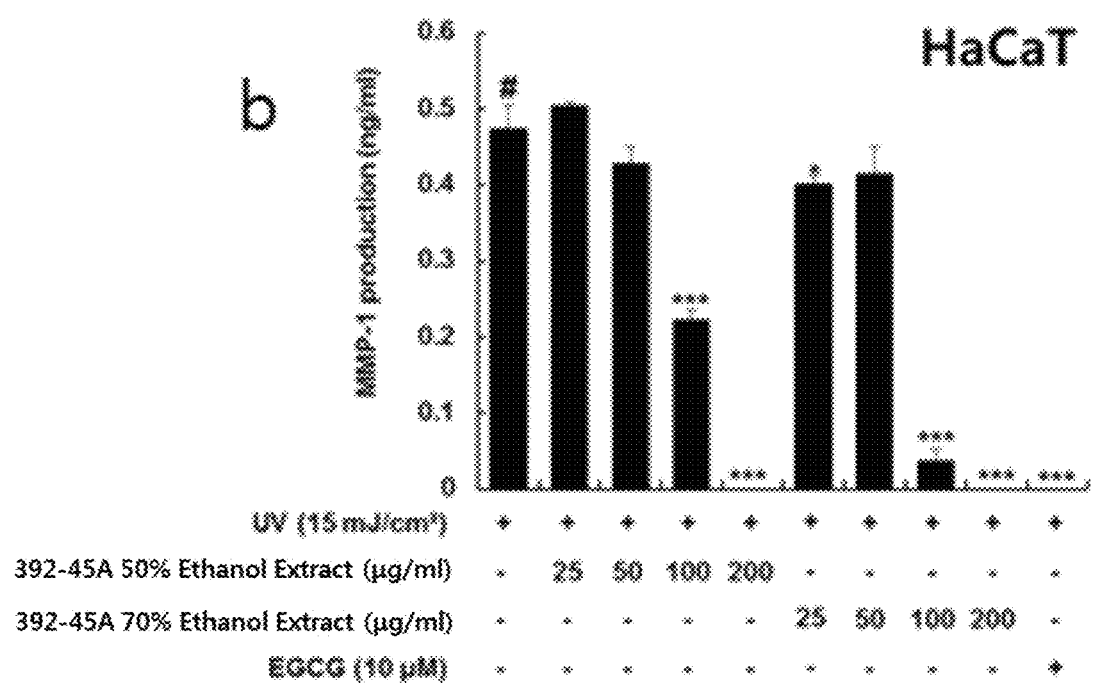
Figure 10C:
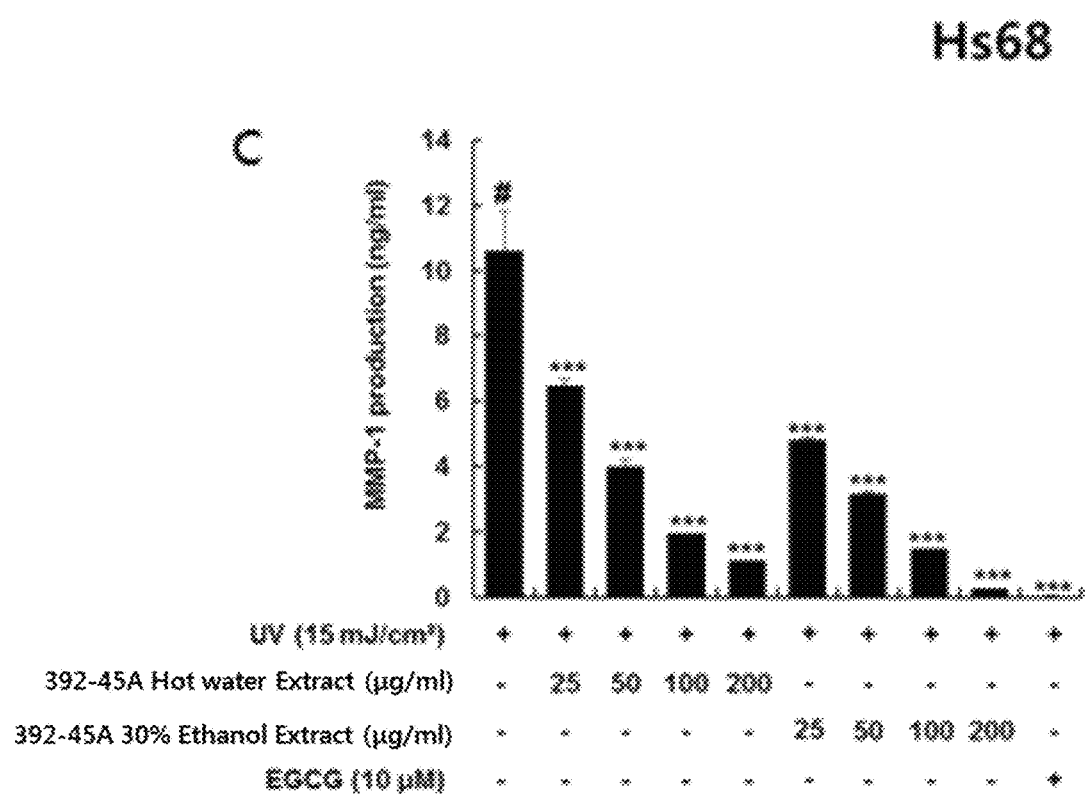
Figure 10D:
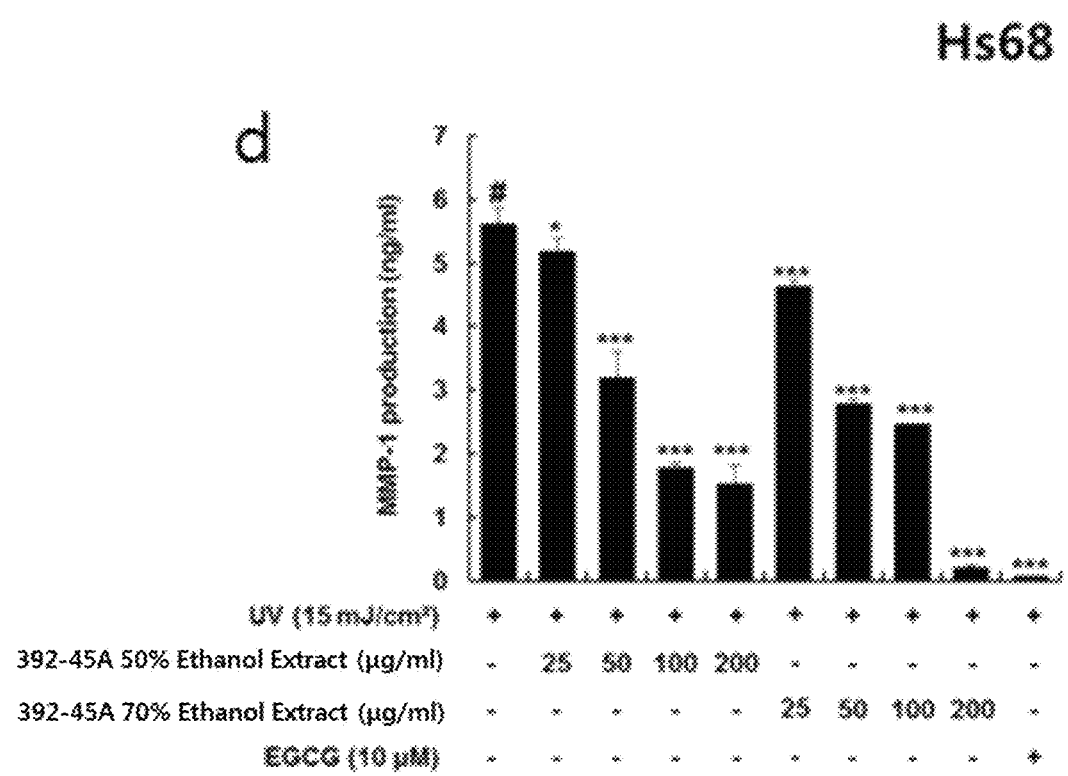

As shown in FIG. 8, the extracts of Example 1 was all non-cytotoxic to the epidermal and dermal cells damaged by UV-B radiation of 15 $mJ/cm^2$ and mostly effective in promoting proliferation of the most of the cells. Especially, the dermal cells treated with the extracts of Example 1 had a similar level of proliferation to those with 10 μM epigallocatechin gallate (EGCG) used as a positive control. Taking the EGCG being a single substance under consideration, the extracts of Example 1 presumably contained a beneficial ingredient more effective in improving UV-induced skin damage. As shown in FIG. 9, the hydrangenol of Example 2 was non-cytotoxic and effective in promoting cell proliferation in the epidermal and dermal cells damaged by UV-B radiation of 15 $mJ/cm_2$. In particular, 1 μM hydrangenol was equivalent to 10 μM EGCG in the cell proliferation effect. In relation to the EGCG with a concentration of 10 μM, the hydrangenol, even with a low concentration, was able to make an excellent effect in preventing or improving UV-induced skin damage.

Experimental Example 2: Quantitative Analysis of MMP-1

Samples obtained in Examples 1 and 2 were measured in regards to the inhibitory effect against the secretion of MMP-1 in epidermal HaCat keratinocytes and dermal Hs68 fibroblasts. In order to evaluate the effect of each sample in reducing MMP-1, the cells were seeded into a 24-well microplate at a density of $1.0 \times 10^5$ cells/well and stabilized for 24 hours. Next, the culture medium was exchanged to a new one supplemented with the sample, and the cells were incubated for 24 hours. For UV-B irradiation, the culture medium was removed, washed with PBS, and exposed to UV-B radiation at 15 $mJ/cm^2$. After an incubation of 48 hours in a culture medium supplemented with the sample, the resultant supernatant was measured in regards to the degree of secretion of MMP-1 by using an MMP-1 Human ELISA kit (ab100603, abcam, US).

Figure 11:
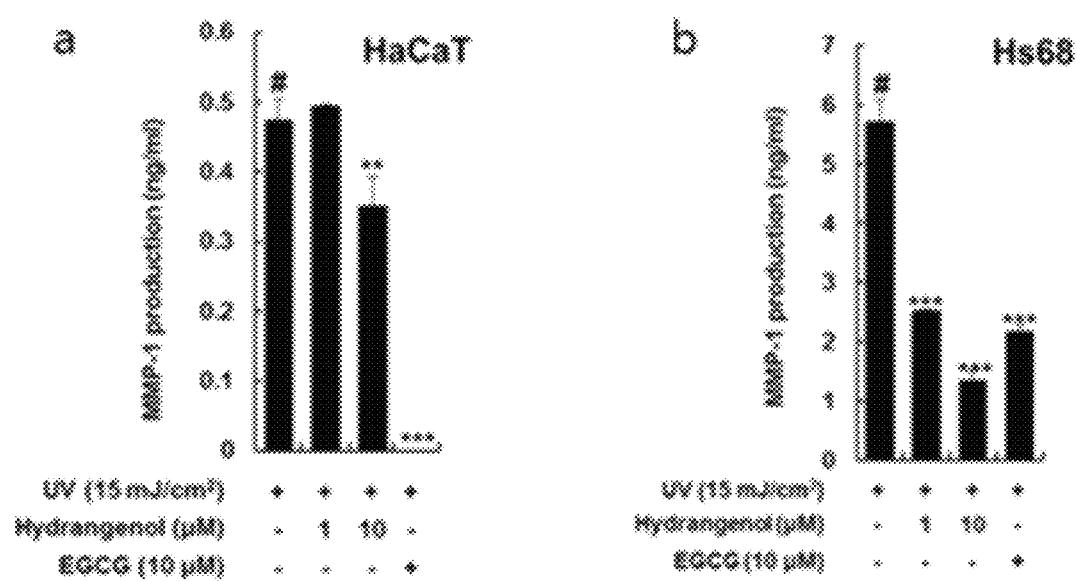
FIG. 11 is a graph showing the inhibitory effect of hydrangenol against MMP-1 in epidermal and dermal cells damaged by UV exposure.

As shown in FIG. 10, all the extracts of Example 1 reduced the production of MMP-1 in a concentration-dependent manner in the epidermal and dermal cells damaged by UV-B radiation of 15 $mJ/cm^2$. As shown in FIG. 11, the hydrangenol of Example 2 also inhibited the production of MMP-1 in a concentration-dependent manner in the epidermal and dermal cells damaged by UV-B radiation of 15 $mJ/cm^2$. Particularly, in the dermal cells, the hydrangenol was far superior to the EGCG at a same concentration in terms of the inhibitory effect against the production of MMP-1. Therefore, it was implied that the hydrangenol of Example 2 was effective in improving UV-induced skin damage by inhibiting the production of MMP-1 incurred by UV exposure.

Experimental Example 3: Analysis of Procollagen Type-1 Content

Samples obtained in Examples 1 or 2 were measured in regards to the effect of increasing procollagen type 1 in dermal Hs68 fibroblasts. In order to evaluate the effect of each sample in increasing secretion of procollagen type 1, the cells were seeded into a 24-well microplate at a density of $1.0 \times 10^5$ cells/well and stabilized for 24 hours. Next, the culture medium was exchanged to a new one supplemented with the sample, and the cells were incubated for 24 hours. For UV-B irradiation, the culture medium was removed, washed with PBS, and exposed to UV-B radiation at 15 $mJ/cm^2$. After an incubation of 48 hours in a culture medium supplemented with the sample, the resultant supernatant was measured in regards to the degree of secretion of procollagen type 1 by using a Procollagen type 1 C-peptide (PIP) EIA kit (Mk101, Takara, Japan).

Figure 12A:
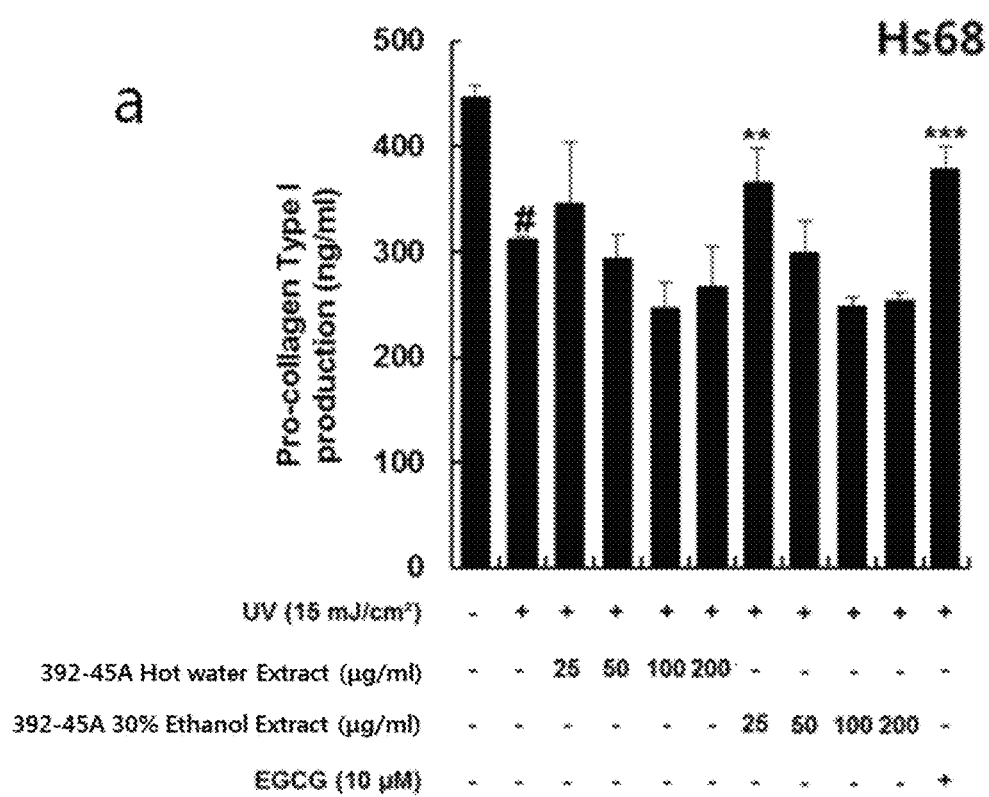
FIGS. 12A and 12B are a graph comparing the production yield of procollagen by the action of the solvent-specific extracts of *Hydrangea serrata* in dermal cells damaged by UV exposure.
Figure 12B:
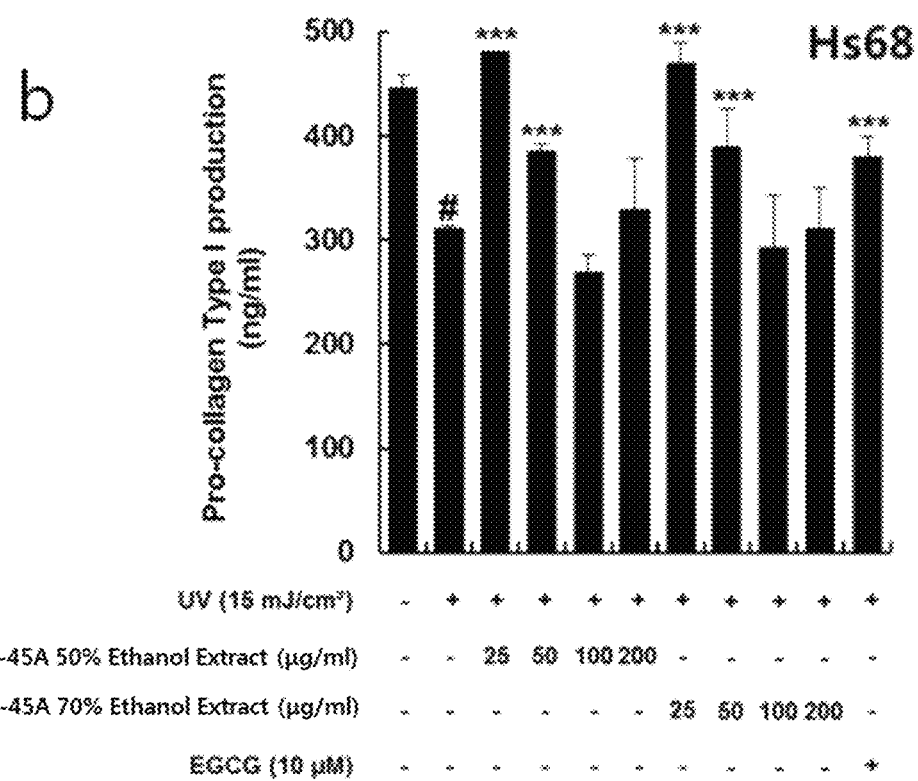
Figure 13:
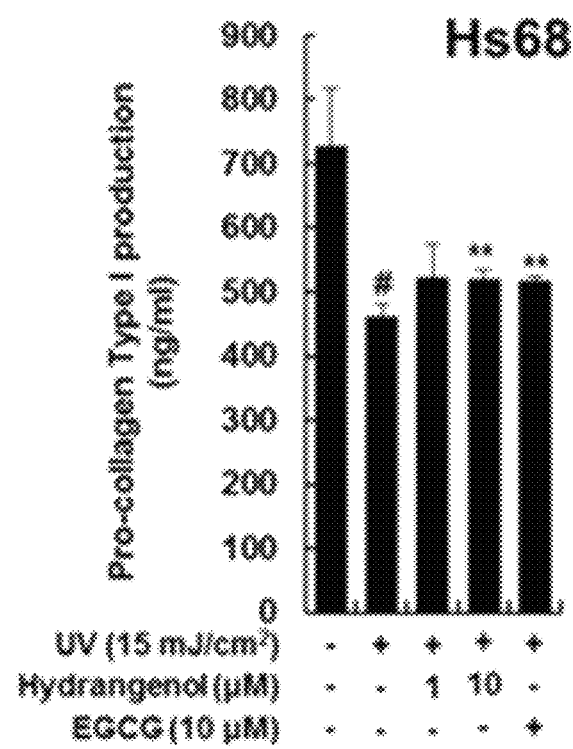
FIG. 13 is a graph showing the production yield of procollagen by the action of hydrangenol in dermal cells damaged by UV exposure.
Figure 14A:
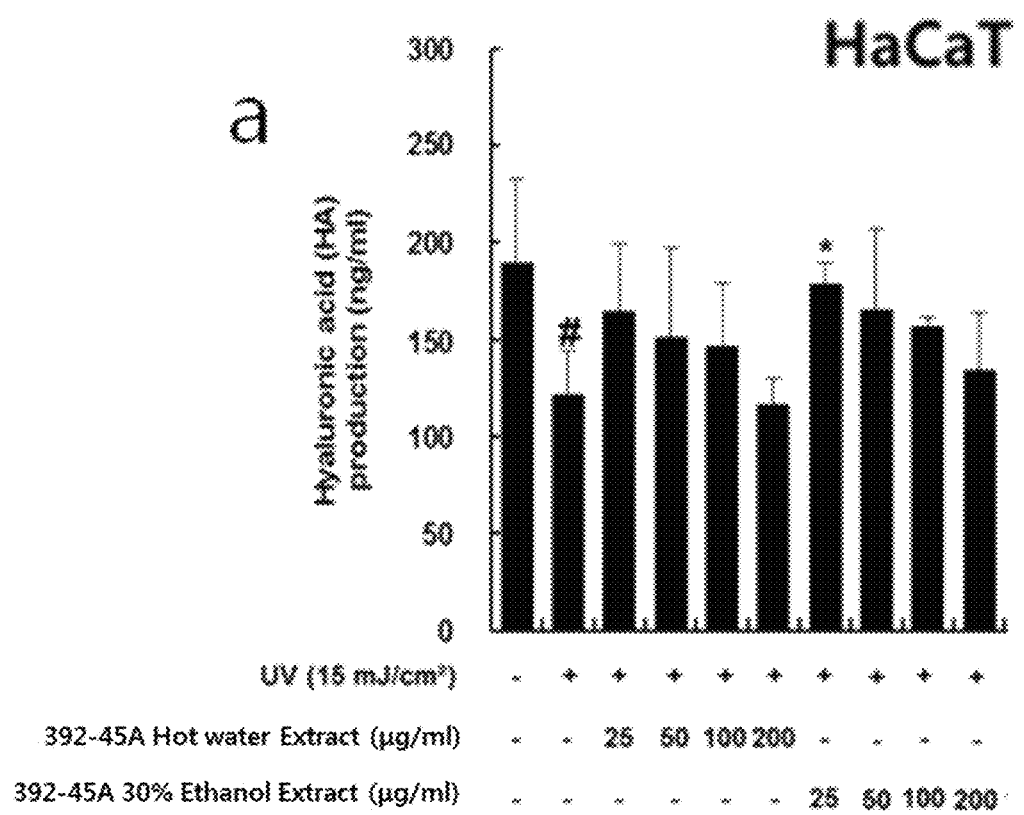
FIGS. 14A to 14D are a graph showing the production yield of hyaluronic acid by the action of the solvent-specific extracts of *Hydrangea serrata* in epidermal and dermal cells damaged by UV exposure.
Figure 14B:
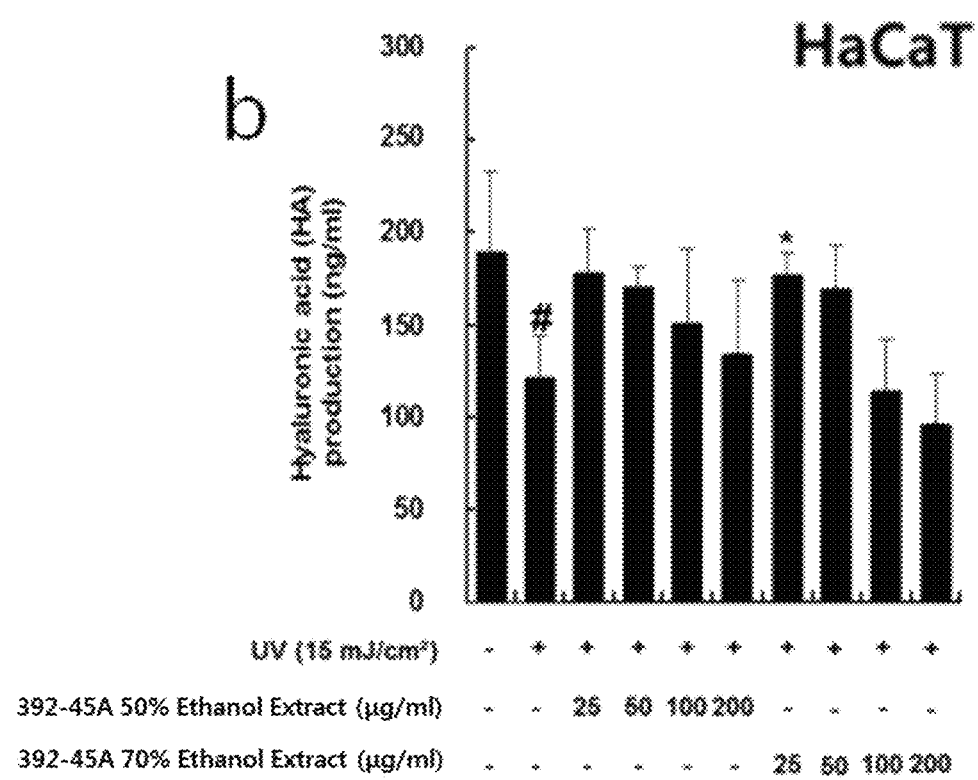
Figure 14C:
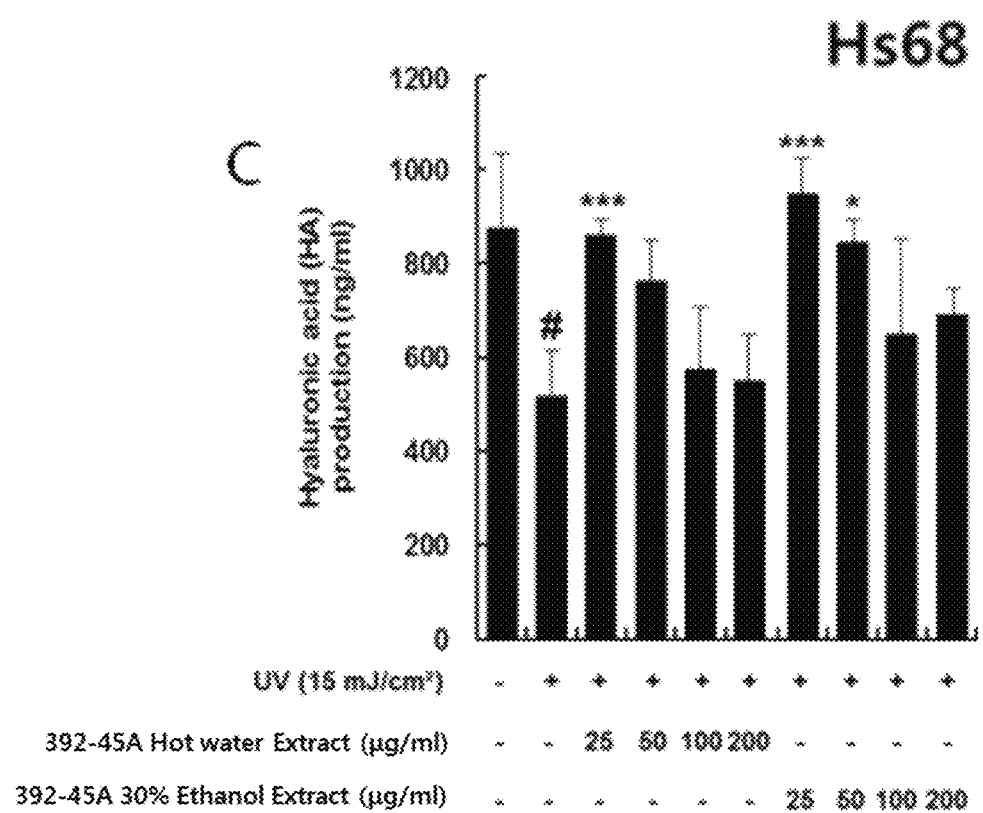
Figure 14D:
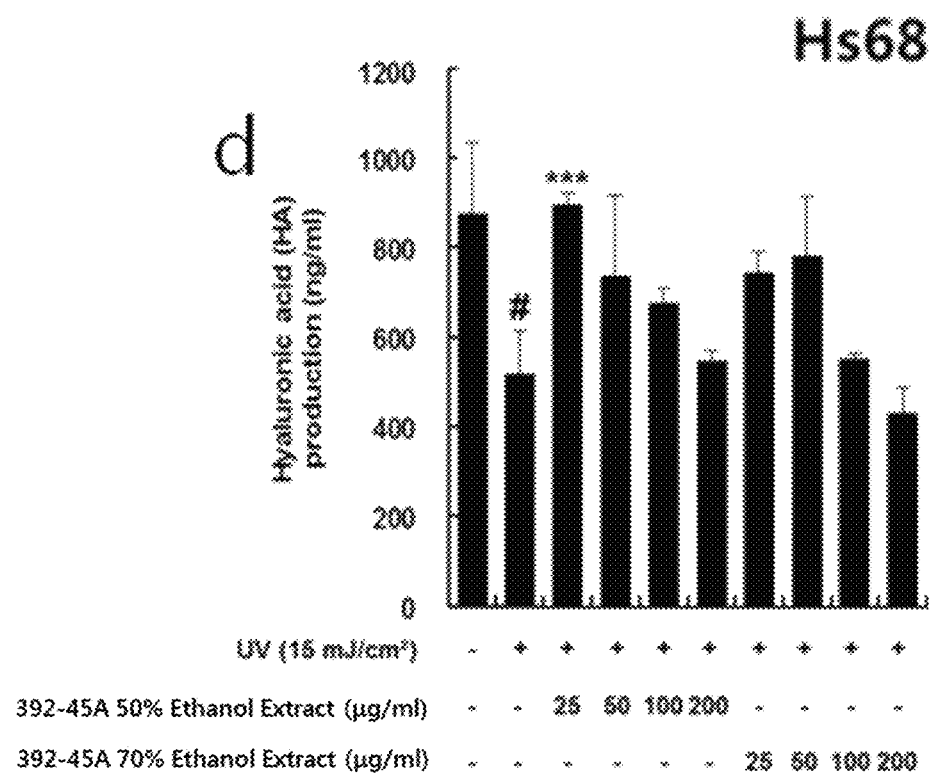

As shown in FIG. 12, all the extracts of Example 1 increased the production of procollagen in the dermal cells damaged by UV-B radiation of 15 $mJ/cm^2$. 50% and 70% extracts were particularly superior to a single substance, EGCG, in the efficacy of procollagen production (Refer to FIG. 12-*b*). On account of this, the extracts of Example 1 presumably contained a beneficial ingredient for skin elasticity. As shown in FIG. 13, the hydrangenol of Example 2 increased the production of procollagen in the dermal cells damaged by UV-B radiation of 15 $mJ/cm^2$. In particular, 1 μM hydrangenol was equivalent to 10 μM EGCG in the procollagen production effect. In relation to the EGCG with a concentration of 10 μM, the hydrangenol, even with a low concentration, was able to make an excellent effect in promoting production of procollagen. Therefore, the hydrangenol of Example 2 proved to increase the production of procollagen and aid the regeneration of collagen fibers degraded by UV radiation, thereby preventing or improving UV-induced skin damage.

Experimental Example 4: Analysis of Hyaluronic Acid Content

Samples obtained in Examples 1 and 2 were measured in regards to the effect of increasing hyaluronic acid in epidermal HaCaT keratinocytes and dermal Hs68 fibroblasts. In order to evaluate the effect of each sample in increasing hyaluronic acid, the cells were seeded into a 24-well microplate at a density of $1.0 \times 10^5$ cells/well and stabilized for 24 hours. Next, the culture medium was exchanged to a new one supplemented with the sample, and the cells were incubated for 24 hours. For UV-B irradiation, the culture medium was removed, washed with PBS, and exposed to UV-B radiation at 15 mJ/cm². After an incubation of 24 hours in a culture medium supplemented with the sample, the resultant supernatant was measured in regards to the degree of secretion of hyaluronic acid by using a TECOR Hyaluronic Acid PLUS ELISA kit (TE 1018-2, TECO Medical Group, US).

Figure 15:
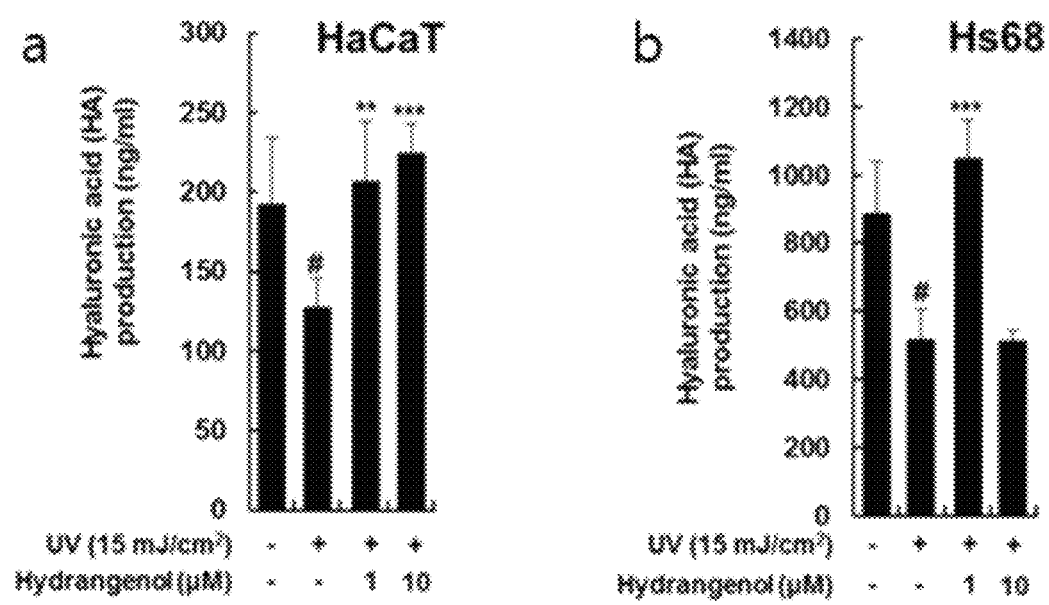
FIG. 15 is a graph showing the production yield of hyaluronic acid by the action of hydrangenol in epidermal and dermal cells damaged by UV exposure.

As shown in FIG. 14, all the extracts of Example 1 increased the production of hyaluronic acid in the epidermal and dermal cells damaged by UV-B radiation of 15 mJ/cm². Particularly in the dermal cells, most of the extracts, even with the lowest concentration, showed an excellent effect of promoting hyaluronic acid. As shown in FIG. 15, the hydrangenol of Example 2 also increased the production of hyaluronic acid in the epidermal and dermal cells damaged by UV-B radiation of 15 mJ/cm². In particular, 1 µM hydrangenol exhibited an excellent effect in producing hyaluronic acid. Accordingly, the hydrangenol of Example 2 proved to increase the production of hyaluronic acid and aid the moisturization of the skin, thereby preventing or improving UV-induced skin damage.

Formulation Example 1: Preparation of Tablets

The extract of Example 2 was mixed with the ingredients of Table 1 and processed into tablets according to a general preparation method for tablet.

TABLE 1

| Ingredients | Unit weight (mg) |
|---|---|
| Example 2 | 10 |
| Corn starch | 100 |
| Lactose | 100 |
| Stearic acid | 2 |

Formulation Example 2: Preparation of Capsules

The extract of Example 2 was mixed with the ingredients of Table 2 and filled in gelatin capsules to prepare soft capsules according to a general preparation method for capsule.

TABLE 2

| Ingredients | Unit weight (mg) |
|---|---|
| Example 2 | 2 |
| Vitamin E | 2.25 |
| Vitamin C | 2.25 |
| Palm oil | 0.5 |
| Vegetable hydrogenated oil | 2 |
| Yellow lead | 1 |
| Lecithin | 2.25 |
| Filling solution for soft capsule | 387.75 |

Formulation Example 3: Preparation of Liquid

The extract of Example 2 was mixed with the ingredients of Table 3 and filled in a bottle or a pouch to prepare a liquid according to a general preparation method for beverage.

TABLE 3

| Ingredients | Unit weight (g) |
|---|---|
| Example 2 | 0.0205 |
| Xanthan gum | 0.0075 |
| Fructooligosaccharide | 0.7500 |
| Powdered coconut flower nectar | 1.0500 |
| Concentrated ssangwha-tang | 1.5000 |
| Red ginseng flavor | 0.0450 |
| Purified water | 20.1425 |
| Filling solution for soft capsule | 387.75 |

Formulation Example 4: Preparation of Chewable Gel

The extract of Example 2 was mixed with the ingredients of Table 4 and filled in a three-sided seal pouch to prepare a chewable gel according to a general preparation method for chewable gel.

TABLE 4

| Ingredients | Unit weight (g) |
|---|---|
| Example 2 | 0.0200 |
| Food gel | 0.3600 |
| Carrageenan | 0.0600 |
| Calcium lactate | 0.1000 |
| Sodium citrate | 0.0600 |
| Complex scutellaria extract | 0.0200 |
| Enzymatically modified stevia | 0.0440 |
| Fructooligosaccharide | 5.0000 |
| Red grape concentrate | 2.4000 |
| Purified water | 13.9560 |

Formulation Example 5: Preparation of Chewable Gel

The extract of Example 2 was processed into the composition of Table 5 according to a general preparation method for nutrient cream.

TABLE 5

| Ingredients | Content (%) |
|---|---|
| Example 2 | 0.01 |
| Sitosterol | 4.0 |
| Polyglyceryl 2-oleate 3.0 | 3.0 |
| Ceteareth-4 | 2.0 |
| Cholesterol | 3.0 |
| Dicetyl phosphate | 0.4 |
| Concentrated glycerin | 5.0 |
| Sunflower oil | 22.0 |
| Carboxylvinyl polymer | 0.5 |
| Triethanol amine | 0.5 |
| Preservative | trace |
| Flavor | trace |
| Purified water | balance |

The above-defined composition is given as a formulation example using a mixture of appropriate compositions. Yet the mixing ratio and the ingredients may be varied arbitrarily under necessity.

The extract of the present invention was stable under the testing conditions for all formulation examples and hence not problematic in the stability of the dosage form.

INDUSTRIAL AVAILABILITY

As described above, the composition containing hydrangenol derived from the extract of *Hydrangea serrata* according to the present invention is able to reduce secretion of MMP-1 produced by UV-B exposure and increase secretion of hyaluronic acid and procollagen type-1, thereby preventing UV-induced skin aging and maintaining skin elasticity. Accordingly, the composition of the present invention is usefully available as a drug, food or cosmetic composition.

What is claimed is:

1. A method for preventing or improving UV-induced skin damage of a subject in need thereof, the method comprising: administering to the subject an effective amount of a composition containing hydrangenol represented by the following chemical formula 1 as an active ingredient:

[Chemical Formula 1]

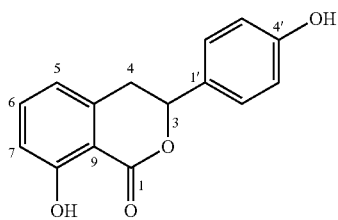

wherein the hydrangenol prevents or improves UV-induced skin damage of the subject by accelerating proliferation of skin cells damaged by UV radiation, reducing production of MMP-1, and increasing production of procollagen and hyaluronic acid.

2. The method as claimed in claim 1, wherein the hydrangenol is isolated from an extract of leaf of *Hydrangea serrata*.

3. The method as claimed in claim 2, wherein the hydrangenol is obtained by ethanol extraction of leaf of *Hydrangea serrata*, ethanol or methanol solvent fractionation, and recrystallization.

4. The method as claimed in claim 1, wherein the hydrangenol is contained in an amount of 0.0001 to 10 wt. % with respect to the total weight of the composition.

5. The method as claimed in claim 1, wherein the composition is used to moisturize the skin irritated by UV radiation or improve wrinkles.

6. The method as claimed in claim 1, wherein the composition is for oral administration and has at least one dosage form selected from the group consisting of tablet, granule, pill, capsule, liquid, chewable gel, and gum.

7. The method as claimed in claim 1, wherein the composition is for topical administration on the skin and has at least one dosage form selected from the group consisting of toner, essence, nutrition cream, moisturizing cream, gel, lotion, and ointment.

8. The method as claimed in claim 1, wherein the composition is a quasi-drug, drug, food, or cosmetic composition.

* * * * *